(12) United States Patent
Roe (10) Patent No.: US 8,920,455 B2
(45) Date of Patent: *Dec. 30, 2014

(54) COLLECTING TECHNIQUE AND DEVICE TO CONCENTRATE A BLOOD SAMPLE ON A TEST PAD

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/279,399

(22) Filed: Oct. 24, 2011

(65) Prior Publication Data

US 2013/0103069 A1     Apr. 25, 2013

(51) Int. Cl.
| | | |
|---|---|---|
| A61B 17/14 | (2006.01) | |
| A61B 17/32 | (2006.01) | |
| A61B 5/151 | (2006.01) | |
| A61B 5/15 | (2006.01) | |

(52) U.S. Cl.
CPC ........... *A61B 5/1411* (2013.01); *A61B 5/15151* (2013.01); *A61B 5/1513* (2013.01); *A61B 5/150412* (2013.01); *A61B 5/15045* (2013.01); *A61B 5/15161* (2013.01); *A61B 5/150358* (2013.01); *A61B 5/150465* (2013.01); *A61B 5/150022* (2013.01); *A61B 5/150511* (2013.01); *A61B 5/150175* (2013.01); *A61B 5/150167* (2013.01)
USPC ....................................................... 606/181

(58) Field of Classification Search
USPC .................. 600/573, 583, 584; 604/264, 272; 606/167, 170, 181–183; 29/557
See application file for complete search history.

(56) References Cited

U.S. PATENT DOCUMENTS

| | | | | |
|---|---|---|---|---|
| 3,060,937 | A * | 10/1962 | Griffitts et al. | 606/181 |
| 7,790,219 | B2 | 9/2010 | Daniel | |
| 2003/0018282 | A1* | 1/2003 | Effenhauser et al. | 600/583 |
| 2003/0087309 | A1 | 5/2003 | Chen | |
| 2005/0228313 | A1* | 10/2005 | Kaler et al. | 600/583 |
| 2006/0030789 | A1 | 2/2006 | Allen | |
| 2006/0178687 | A1* | 8/2006 | Freeman et al. | 606/181 |
| 2007/0003448 | A1 | 1/2007 | Kanigan et al. | |
| 2008/0103415 | A1* | 5/2008 | Roe et al. | 600/583 |
| 2009/0192409 | A1* | 7/2009 | Wong et al. | 600/583 |
| 2013/0006147 | A1* | 1/2013 | Fukuda | 600/573 |

FOREIGN PATENT DOCUMENTS

| | | | |
|---|---|---|---|
| EP | 1360932 A1 | | 12/2003 |
| JP | 2011183076 A | * | 9/2011 |
| WO | 2011111580 A1 | | 2/2011 |

* cited by examiner

*Primary Examiner* — Katherine M Shi (74) *Attorney, Agent, or Firm* — Dinsmore & Shohl LLP (57) ABSTRACT

A lancet structure for making an incision at a skin site and transporting an amount of blood from the incision away from the skin site and methods of utilizing and making such a lancet structure are disclosed. The lancet structure may comprise an elongated body having a first surface and a second surface, a skin penetrating end for making the incision, a through bore extending from the first surface to the second surface, and a blood transport portion extending from the skin penetrating end to the through bore along the first surface. The blood transport portion is configured to transport the amount of blood away from the skin site via a capillary force to the through bore, and the through bore is configured to transport the blood to the second surface.

37 Claims, 6 Drawing Sheets

COLLECTING TECHNIQUE AND DEVICE TO CONCENTRATE A BLOOD SAMPLE ON A TEST PAD

TECHNICAL FIELD

The present disclosure relates generally to obtaining body fluid samples, and more particularly, to a collecting technique and device to concentrate a blood sample on a test pad.

BACKGROUND

Portable handheld medical diagnostic devices are often employed to measure concentrations of biologically significant components of bodily fluids, such as, for example, glucose concentration in blood. The portable handheld medical diagnostic devices and their accessories may work together to measure the amount of glucose in blood and be used to monitor blood glucose in one's home, healthcare facility or other location, for example, by persons having diabetes or by a healthcare professional. Some of the most economical portable handheld medical diagnostic devices are those which provide such measurements via LED-photodiode detection techniques.

For people with diabetes, regular testing of blood glucose level can be an important part of diabetes management. In particular, self-monitoring of blood glucose may require the patient to use a lancet to prick a skin site, typically, a finger for a drop of blood which is provided to a portable handheld medical diagnostic device for testing. Patients may need to repeat this process several times a day. However, due to the sensitivity of the fingertips, repeat testing can be quite painful and even traumatic for many users, especially among children and infants.

It is to be appreciated that the smaller the sample amount needed to be used by such devices in order to determine a result, such as a blood glucose level, the smaller and/or shallower the incision made by the lancet is needed, thus resulting in less pain and trauma for the user. However, in conventional portable handheld medical diagnostic devices which measure the amount of glucose in blood via LED-photodiode detection techniques, the sample amount (e.g., greater than 90 nanoliters) needed by such devices results in an incision from a lancet size which still provides some pain and/or trauma to users. Accordingly, there continues to be a need for an improved lancet structure which provides minimum pain and trauma to users by concentrating a correspondingly small blood sample (about 90 nanoliters or less) on a test pad such that a LED-photodiode detection technique employed by of a medical diagnostic device may be used more comfortably by users.

SUMMARY

In one embodiment, a lancet structure for making an incision at a skin site and transporting an amount of blood from the incision away from the skin site is disclosed. The lancet structure may comprise an elongated body having a first surface and a second surface, a skin penetrating end for making the incision, a through bore extending from the first surface to the second surface, and a blood transport portion extending from the skin penetrating end to the through bore along the first surface. The blood transport portion is configured to transport the amount of blood away from the skin site via a capillary force to the through bore, and the through bore is configured to transport the blood to the second surface.

In another embodiment, a method of forming a lancet structure which is used for making an incision at a skin site and transporting an amount of blood from the incision away from the skin site is disclosed. The method may comprise providing an elongated body having a first surface and a second surface, forming a skin penetrating end for making the incision in the body, and forming a through bore which extends from the first surface to the second surface. The method may further comprise forming a blood transport portion extending from the skin penetrating end to the through bore along the first surface. The blood transport portion being configured to transport the amount of blood away from the skin site via a capillary force to the through bore, and the through bore being configured to transport the blood to the second surface.

These and other advantages and features of the various embodiments of the invention disclosed herein, will be made more apparent from the description, drawings and claims that follow.

BRIEF DESCRIPTION OF THE DRAWINGS

The following detailed description of the exemplary embodiments of the present invention can be best understood when read in conjunction with the following drawings, where like structure is indicated with like reference numerals, and in which.

DETAILED DESCRIPTION

The following description of hereinafter disclosed embodiments is merely exemplary in nature and is in no way intended to limit the invention or its application or uses. Likewise, skilled artisans appreciate that elements in the figures are illustrated for simplicity and clarity and have not necessarily been drawn to scale. For example, the dimensions of some of the elements in the figures may be exaggerated relative to other elements to help to improve understanding of the various embodiments of the present invention.

Figure 1:
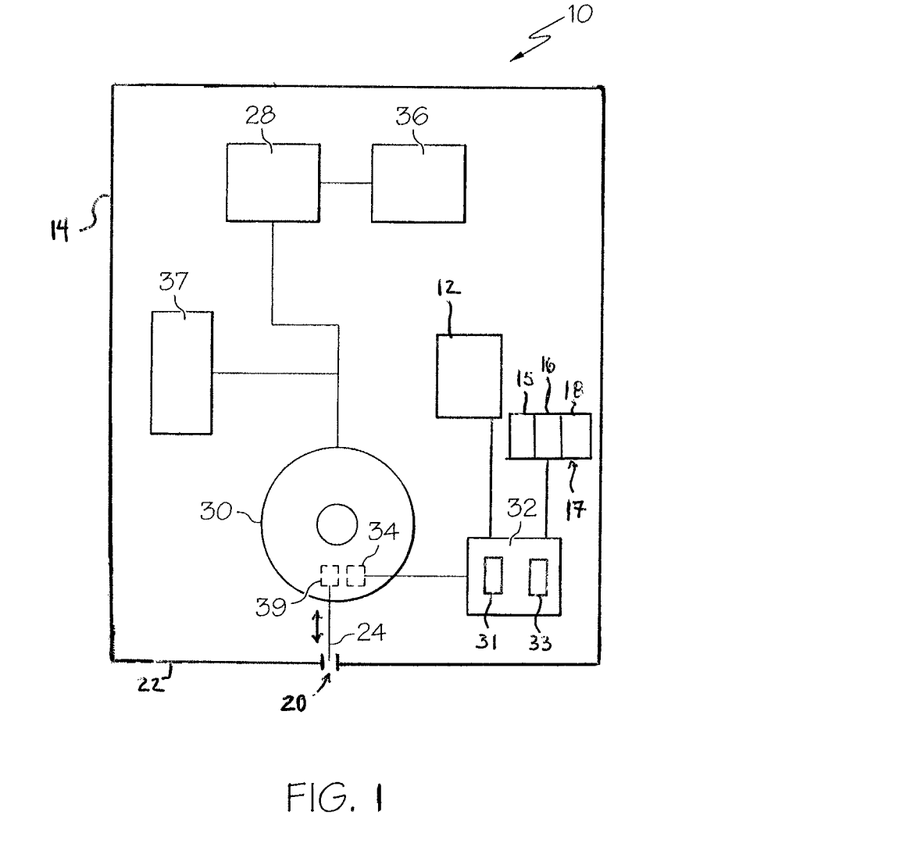
FIG. 1 is a schematic representation of a portable handheld medical diagnostic device.

Referring to FIG. 1, a simplified, schematic view of a medical diagnostic device 10 is depicted. In one embodiment, the medical diagnostic device 10 is an in vitro diagnostic device that is used to test blood and other body fluids and tissues to obtain information for the diagnosis, prevention and treatment of a disease. The medical diagnostic device 10 may be a self-testing blood glucose meter for people with diabetes. In one embodiment, the medical diagnostic device 10 is a handheld reagent-based blood glucose meter, which measures glucose concentration by observing some aspect of a chemical reaction between a reagent and the glucose in a fluid sample. The reagent may be a chemical compound that is known to react with glucose in a predictable manner, enabling the monitor to determine the concentration of glucose in the sample. For example, the medical diagnostic device 10 may be configured to measure a voltage or a current generated by the reaction between the glucose and the reagent in one embodiment, electrical resistance in another embodiment, as well as a color change of the reagent in still another embodiment.

In general, the illustrated portable, handheld medical diagnostic device 10 includes a display device 12 provide in and viewable through a protective enclosure 14, which also protects electronics and other mechanical components therein. The protective enclosure 14 is somewhat rectangular in shape; however, any other suitable shapes may be used for the protective enclosure, such as circular shapes, etc. The display device 12 may be any suitable display device used in a portable, handheld electronic device, such as, for example, but not limited to LCD display devices, LED display devices, OLED display devices, and other types of display devices which may be heretofore developed. Further, display device 12 may be any other variety of indicators, including, but not limited to a series of lights and/or other types of light devices as opposed to a single integrated display screen. In one embodiment, the display device 12 includes an electronic paper component such as an electrophoretic display, which may be an information display that forms visible images by rearranging charged pigment particles using an electric field. The display device 12 may be used for electronically displaying graphics, text, and other elements to a user. In some embodiments, the display device 12 may be a touch-screen user interface that is used with the tip of a finger of the user and/or a stylus or other touching device to select elements from the screen, to draw figures, and to enter text with a character recognition program running on the device 10. In some embodiments, the medical diagnostic device 10 may also include other types of output devices such as for example, sound devices, vibration devices, etc.

The medical diagnostic device 10 further includes a user interface (generally referred to by reference symbol 17), which may include buttons 15, 16 and 18. The buttons 15, 16 and 18 may be used by an operator, for example, to view data stored in memory (not shown) of the medical diagnostic device 10, adjust settings of the device and scroll through test results. The buttons 15, 16 and 18 may be manually actuated, such as by pressing the buttons. The buttons 15, 16 and 18 may comprise touch sensors (e.g., resistive or capacitive touch sensors, surface acoustic wave sensors, infrared LED, photodetectors, piezoelectric transducers, etc.) that can be actuated by placing and/or pressing a tip of the finger within the button areas. In these embodiments, the buttons 15, 16 and 18 may not move. Instead, the buttons 15, 16 and 18 may be indicated visually to identify where to place the finger. In other embodiments utilizing touch sensors, the buttons 15, 16 and 18 may move, for example, to bring the finger or touching device into close proximity to the touch sensor. In some embodiments, the medical diagnostic device 10 may provide other button or input types such as an OK button and/or joy stick/track ball, which a user may utilize to navigate through a software drive menu provided on the display device 12. Additional buttons may be used as shortcut buttons, for example, to call up a certain program on the medical diagnostic device 10, as a method of scrolling, to select items from a list, or to provide any function that the software designer of the device may assign to the button or set of buttons. Each button size, layout, location, and function may vary for each manufacturer and model of the medical diagnostic device 10.

A lancet port 20 is located at a bottom portion 22 of the medical diagnostic device 10. The lancet port 20 provides an opening through which a lancet structure 24 can extend outwardly from the protective enclosure 14. The lancet structure 24 may extend outwardly from the lancet port 20 to make an incision at a skin site of the patient and produce an amount of blood from the skin site of the patient.

In general, the medical diagnostic device 10 may include a lancet housing assembly 30 in the form of a cartridge or disk that is used to house multiple ones of the lancet structure 24 for use in the medical diagnostic device 10, a lancet actuator assembly 28 for extending and/or retracting the lancet structures 24 and a speed control mechanism 36 that engages the lancet actuator assembly 28 for adjusting the speed at which the lancet structure 24 is extended and/or retracted by the lancet actuator assembly 28. A depth adjustment mechanism 37 may also be provided that allows for adjustment of a penetration depth of the lancet structure 24 before extending the lancet structure 24.

A measurement system 32 providing a processor 31 for measuring a feature of a bodily fluid sample supplied to the device 10 is also provided in the protective enclosure 14. For example, in one embodiment, the measurement system 32 may be of the type that measures glucose concentration in a blood sample delivered to a test material or test pad 39, for example, using an optical device 34 in one embodiment for detecting a color change in a reagent or other suitable device in other embodiments, such as electrical contacts if measuring a change in an electrical characteristic/property of the reagent. The test pad 39 may be employed to hold the reagent and to host the reaction between the glucose and the reagent mentioned above.

In one embodiment, the test pad 39 and the optical device 34 may be located such that the reaction between the glucose and the reagent may be read electronically in order for the measurement system 32 to determine the concentration of glucose in the blood sample and display the results to a user using the display device 12. These embodiments enable both health care professionals and patients to perform reliable decentralized testing in hospitals, clinics, offices or patients' homes.

In one particular embodiment, the measurement system 32 detects a color change of a dry reagent when contacted with a bodily fluid sample, such as blood, that has been provided to the test pad 39. In one embodiment a blood sample is provided to the test pad 39 via the lancet structure 24. Further details with regard to a lancet structure for providing a small blood sample (about 90 nanoliters or less) to a test pad such that a medical diagnostic device employing a LED-photodiode detection technique may be used is provided hereafter in a later section. It is to be appreciated that due to the small blood sample size (about 90 nanoliters or less), the corresponding size and/or depth of an incision formed by the improved lancet structure according to one or more embodiments of the present invention may provide minimum pain and trauma to users.

In one embodiment, after the test pad 39 is provided with the blood sample, the test pad 39 is illuminated by the measurement system 32 such that any color change due to the chemical reaction between the sample and the reagent of the test pad 39 is detected by the optical device 34, e.g., a photodiode detector. A resulting detection signal from the optical device 34 is then provided to and processed by the processor 31 of the measurement system 32. The result(s) of the processing by the processor 31 on the received detection signal to determine a characteristic(s) and/or a property(ies) of the provided blood sample may be displayed on the display device 12 and/or stored in memory 33 of the device 10 (or measurement system 32) or maintained by the display device 12 until updated by a next measurement result, as is the case if the display device 12 is an electronic paper based display. In one embodiment, the user interface 17 may be used by the user to select and display testing results stored in memory 33 as well as to communicate with the processor 31 to perform any of the device functions discussed previously above in earlier sections. It is to be appreciated that in other embodiments, the processor 31 and memory 33 as well as the measurement system 32 along with other system components (not shown) such as a display controller and/or display driver, a clock, an analog to digital convertor(s), light(s), power (battery) management controller/functions may be provided as an application specific integrated chip (ASIC), as individual (discrete) components in still other embodiments, or in combinations thereof in still other embodiments. Such components are electrically connected to the processor 31 and all of which are powered by a portable power supply (not shown), such as a battery which may or may not be rechargeable by an A/C adapter, such as in the embodiment of the device 10 being a limited use and disposable device. Other features of a suitable medical diagnostic device are described in co-pending and commonly owned U.S. patent application Ser. No. 12/981,677, filed Dec. 30, 2010, and entitled HANDHELD MEDICAL DIAGNOSTIC DEVICES, the disclosure of which is herein incorporated fully by reference.

Figure 2:
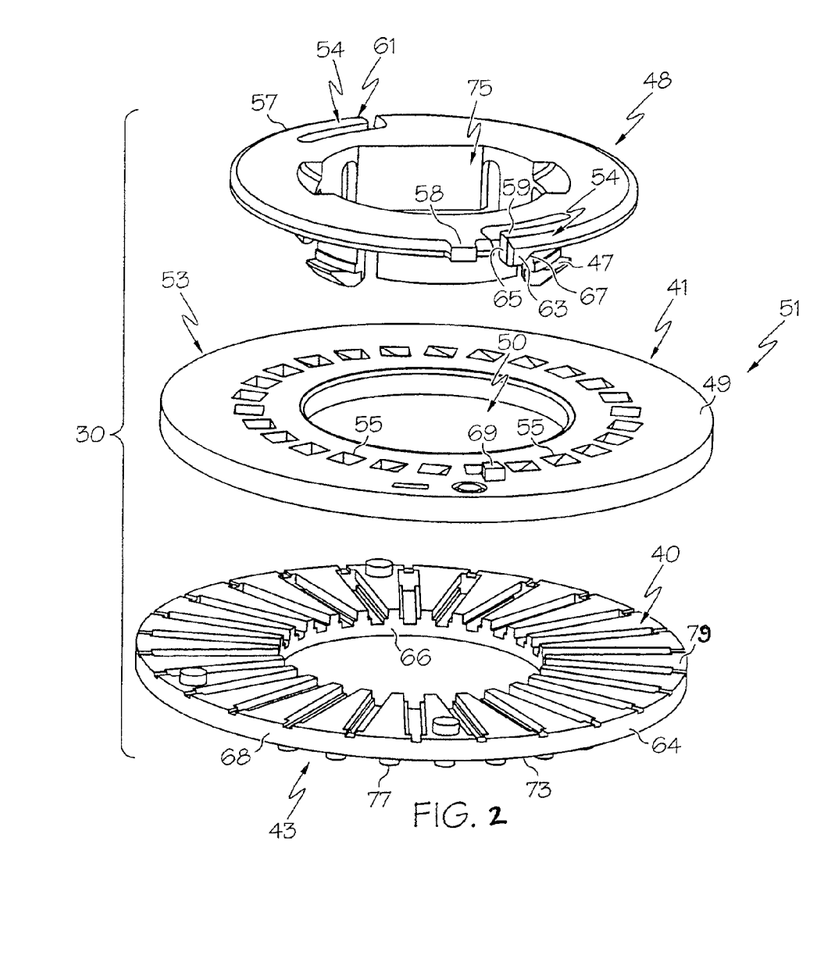
FIG. 2 is an exploded perspective view of a lancet housing assembly suitable for use with the portable handheld medical diagnostic device of FIG. 1 and showing a plurality of lance compartments.

Referring to FIG. 2, in some embodiments, multiple ones of the lancet structure 24 are housed in the lancet housing assembly 30 in the form of a disk that includes multiple lancet compartments 40 (FIG. 5) arranged in a radial fashion about a central axis. The lancet housing assembly 30 may have an outer protective housing (not shown) formed of any one or more suitable materials, such as plastics, foils, metals, and the like. Materials with sterile moisture barriers may be used to provide lancet compartments 40 with protected environments. In some embodiments, such as the one illustrated, the lancet housing assembly 30 may be formed by a center hub 48 and a disk component 51 that is configured to rotate relative to the center hub 48. In some embodiments, the disk component 51 includes an upper disk member 41 and a lower disk member 43 that is connected to the upper disk member 41. Any suitable connection may be used between the upper and lower disk members 41 and 43, such as laser welding, snap fit, press fit, adhesives, fasteners, and the likes.

As depicted in the exploded view of FIG. 2, the center hub 48 may be provided within a central bore 50 of the lancet housing assembly 30 such that it may rotate relative to the disk component 51. In one embodiment, the center hub 48 may be provided such that it may snap fit into place within the central bore 50 of the lancet housing assembly 30. For example, the center hub 48 may include fastening structures 47 in the form of hook-like projections that engage a bottom surface 73 of the disk component 51. Although the center hub 48 may be mounted to rotate within the central bore 50 of the lancet housing assembly 30 such that it may be removably retained therein, such as via the snap fit arrangement depicted in FIG. 2, or via a fastener(s) in another embodiment which provides a nut or clip (not shown) which engages a threaded or shaped end (not shown) of the center hub 48 adjacent the bottom surface 73, in other embodiments the center hub 48 may be provided to rotate therein but also retained permanently therein, such as via laser welding in another embodiment which provides a deformed free end (not shown) of the center hub 48 that flairs outwardly about the bottom surface 73. The center hub 48 may have a non-circular or irregular-shaped (e.g., D-shaped) key or opening 75 that allows for automatic alignment of the lancet housing assembly 30 in only one or more orientations for insertion into a disk compartment 52 of the medical diagnostic device 10. For example, in the illustrated embodiment, the D-shaped key may allow for automatic alignment of the lancet housing assembly 30 in only one orientation for insertion into the disk compartment 52.

The center hub 48 may include rotation limiting structure 54 that cooperates with rotation limiting structure (e.g., the notches 55) of the upper disk member 41. The center hub 48 may include arm members 57 and 59, each having a downward protruding projection 61 and 63 that is sized and arranged to be removably received by the notches 55 as the upper disk member 41 rotates relative to the center hub 48. The projections 61 and 63 may each include a relatively vertically oriented side 65 and a relatively angled side 67 that is at an angle to the vertical. The vertically oriented side 65 can inhibit rotation of the upper disk member 41 relative to the center hub 48 while the angled side 67 allows rotation of the upper disk member 41 relative to the center hub 48 in the opposite direction. The arm members 57 and 59 may be formed of a somewhat flexible material to allow the arm members 57 and 59 to resiliently bend so that the projections 61 and 63 may move out of one notch 55 and be received by an adjacent notch 55 for locking the upper disk member 41 in an angular relationship relative to the center hub 48. Cooperating end stops 58 and 69 may also be provided to prevent rotation of the upper disk member 41 relative to the center hub 48 once the end stops 58 and 69 engage.

The lower disk member 43 includes a top surface 79, a bottom surface 73 opposite the top surface 79, an outer facing side 64 and an inner facing side 66. The lancet compartments 40 extend in a generally radial direction from the inner facing side 66 to the outer facing side 64. The lancet compartments 40 may be equally spaced an angular distance apart from one another and about the periphery of the lower disk member 43. As will be described in greater detail below, each lancet compartment 40 may include a lancet structure 24 that can extend through an opening 68 in each lancet compartment 40 and through the lancet port 20 of the medical diagnostic device 10. Extending downwardly from the bottom surface 73 of the lower disk member 43 are indexing pins 77. The indexing pins 77 may be used to rotate the disk component 51 relative to the center hub 48, for example, after each operation of the lancet structures 24.

Figure 3:
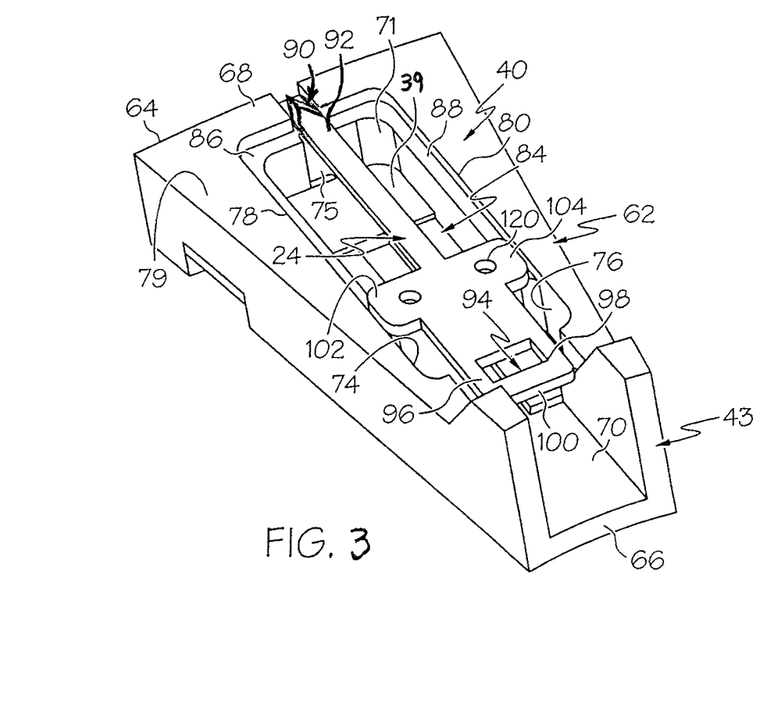
FIG. 3 illustrates is a top perspective view of a lancet compartment of the lancet housing assembly of FIG. 2 with an embodiment of a lancet structure.

Referring to FIG. 3, an exemplary lancet compartment 40 with an unused lancet structure 24 is shown, respectively. The lancet compartment 40 is formed, in part, by a compartment section 62 of the lower disk member 43. The upper disk member 41 is removed in FIG. 3 for clarity. The compartment section 62 includes the outer facing side 64 and the inner facing side 66. The opening 68 is located at the outer facing side 64 that can align with the lancet port 20 located at the bottom 22 of the medical diagnostic device 10 (FIG. 1). Sidewalls 78 and 80 extend between the outer facing side 64 and the inner facing side 66. A clearance floor 70 extends from an inner wall 71 at the outer facing side 64 within the lancet compartment 40 to the inner facing side 66 and forms a lowermost floor of the lancet compartment 40. Adjacent the inner wall 71 of the lancet compartment 40 is the test pad 39, which is located on the clearance floor 70 and within the lancet compartment 40. The test pad 39 may be a test strip such as electrochemical type test strips, colorimetric or optical type test strips, etc., to name a few.

Drop down slots 74 and 76 are located in sidewalls 78 and 80 and extend vertically from the top surface 79 of the compartment section 62 to a lancet floor 84. Another drop down slot 75 is located in the inner wall 71 and extends vertically from the opening 68 to the test pad 39. The lancet floor 84 extends along the clearance floor 70, in a raised relationship thereto, from the test pad 39 back toward the inner facing side 66 and within the drop down slots 74 and 76. In some embodiments, the lancet floor 84 may be formed by a pair of strips 85 and 87 that extend along their respective sidewall 78 and 80 and spaced-apart from each other thereby exposing part of the clearance floor 70 therebetween. In some embodiments, the lancet floor 84 and the clearance floor 70 may both be part of the same floor structure. The lancet floor 84 provides clearance between the clearance floor 70 and the lancet structure 24 when the lancet structure is dropped down against the test pad 39 and seated against the lancet floor 84. Lancet guide rails 86 and 88 extend along the sidewalls 78 and 80 and recessed vertically below the top surface 79 of the compartment section 62. In some embodiments, the lancet guide rails 86 and 88 extend substantially parallel to the lancet floor 84 and/or clearance floor 70 from the drop down slots 74 and 76 to the opening 68 with the drop down slot 75 intersecting the lancet guide rails 86 and 88 at the inner wall 71 and the drop down slots 74 and 76 intersecting the guide rails 86 and 88, respectively, at the sidewalls 78 and 80.

Lancet Structure

The lancet structure 24, in this exemplary embodiment, includes a skin penetrating end 90 and a blood transport portion 92 adjacent the skin penetrating end 90. In some embodiments, the blood transport portion 92 may include one or more capillary structures that facilitate movement of the bodily fluid away from the skin penetrating end to the blood transport portion 92. The skin penetrating end 90, when extended through the opening 68, is shaped and sized to penetrate the patient's skin at a skin site in order to provide an amount of blood. In some embodiments, the skin penetrating end 90 provides a knife edge in which to help penetrate and form an incision in the patient's skin at the skin site. The blood transport portion 92 can receive the amount of blood from the skin penetrating end 90 and be used to carry the amount of blood away from the skin location.

In some embodiments, a connecting structure 94 is located at an end 96 that is opposite the skin penetrating end 90. In the illustrated embodiment, the connecting structure 94 is a closed opening 98 having a rear ledge 100 that is used to engage the lancet actuator assembly 28 (FIG. 1) for extending and/or retracting the lancet structure 24 (e.g., in the form of a drive hook). In other embodiments, the connecting structure 94 may have other shapes, such as an open ended C-shape design, one or more circular or oval holes provided near the end 96, the end 96 providing a connecting shape, such as a T-shape, and the like as long as a releasable connection is provided between the lancet structure and the lancet actuator assembly 28 (FIG. 1). In the illustrated embodiment of FIG. 3, a guiding structure is also provided in the form of outwardly extending wings 102 and 104 which are located between the connecting structure 94 and the blood transport portion 92. The wings 102 and 104 extend outwardly in the widthwise direction to ride along the lancet guide rails 86 and 88 when extending and retracting the lancet structure 24 from its associated lancet compartment 40.

Referring to FIGS. 4-10, various further embodiments of the lancet structure 24 for making an incision at a skin site and transporting an amount of bodily fluid from the incision away from the skin site are disclosed. Generally, in these further embodiments, the lancet structure 24 comprises an elongated body 200 having a first surface 202 (FIG. 4) and a second surface 204 (FIG. 5), the skin penetrating end 90 for making the incision, a through bore 206 extending from the first surface 202 to the second surface 204, and the blood transport portion 92 (FIG. 4) extending from the skin penetrating end 90 to the through bore 206 along the first surface 202. The blood transport portion 92 is configured to transport the amount of bodily fluid away from the skin site via a capillary force to the through bore 206. The through bore 206 as well is configured to transport the bodily fluid to the second surface 204 also via a capillary force.

Spreading Area

Figures 5, 9, 10:
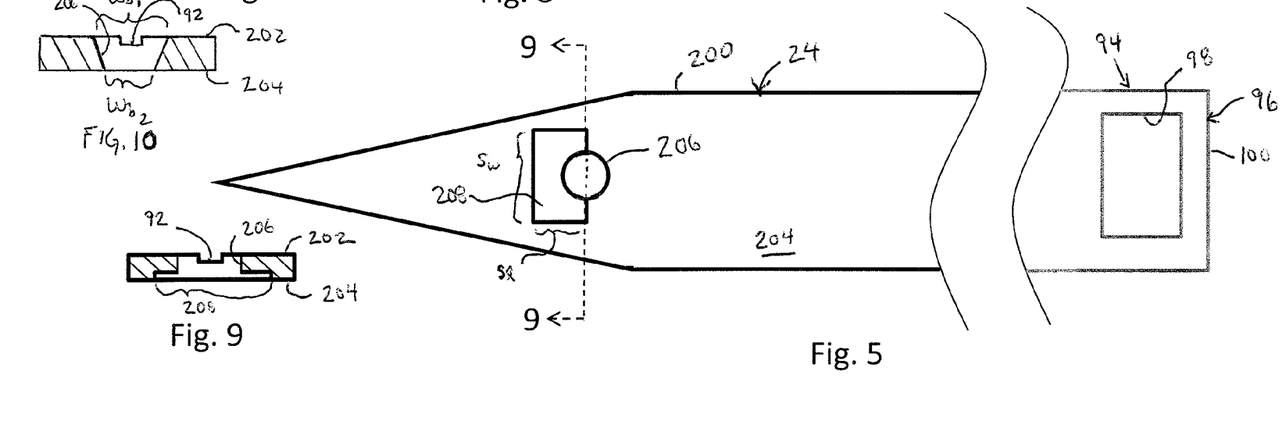
FIG. 5 illustrates a bottom view of an embodiment of a lancet structure suitable for use in the lancet compartment of FIG. 3, and having a top view according to FIG. 4.
FIG. 9 illustrates a cross-sectional view of the lancet structure of FIG. 5 taken along section line 9-9.
FIG. 10 illustrates a cross-sectional view according to another embodiment of the lancet structure of FIG. 4 along a section line similar to section line 8-8.

In some embodiments, provided to the second surface 204 adjacent the through bore 206 is a spreading area 208 (FIG. 5) for increasing the surface area of the blood fluid transported to the second surface 204 via the through bore 206. As can be seen in FIG. 5, the through bore 206 intersects the second surface 204 at a location partially outside the spreading area 204. It is to be appreciated that by spreading out the blood sample drawn to the second surface 204 through the through bore 206, a large surface area of the sample (i.e., a surface area larger than that defined by the through bore 206) is available for contact with a reagent e.g., provided by the test pad 39 (FIG. 3). Due to this large surface area of the sample provided by the lancet structure 24, a corresponding detection area in the test pad 39, which results from the contact of the sample with the test pad, will be substantially filled. As a result of this spreading out of the sample in the spreading area 208 and subsequent filling of the corresponding detection area in the test pad 39 with the sample after contact therebetween, LED-photodiode detection techniques (such as color change detection mentioned above in a previous section) may be used advantageously with such a lancet structure 24 which after making an incision, then needs to transport only about 90 nl or less of the body fluid sample from a skin site of a patient. Accordingly, the incision made by such a lancet structure 24 at the skin site can be smaller and shallower than those made by conventional lancets used with blood testing devices using LED-photodiode detection techniques, and thereby may provide more comfort to users. It is also to be appreciated that due to the spreading area 208, the use of an absorbent material such as a sponge is not needed in the test pad 39 in order to draw in and spread the sample over the defined detection area, thereby simplifying production and reducing costs.

The spreading area 208 can be formed on or from the elongated body 200 so that the sample spreads according to the geometry of the area. The geometry of the spreading area 208 may include rectangular geometries, circular geometries, triangular geometries, polygonal geometries, and combinations thereof. For example, in the illustrated embodiment of FIG. 5, the spreading area 208 has circular and rectangular geometries, but in other embodiments other geometries may be used. In some embodiments, the spreading area 208 has an area the can range from about 0.25 to about 2.0 mm², which provides suitable spreading of the sample for detection in a detection area of the test pad 39 by LED-photodiode detection techniques when the lancet structure 24, after making an incision, transports about 90 nl or less of the body fluid sample from a skin site of a patient.

The formation of the spreading area 208 can result from deposition, such as photolithographic patterning, molding, printing, stamping embossing or etching into the body, or other 200 patterning methods known to one skilled in the art. For example, in some embodiments, the spreading area 208 is defined by etching into the body 200 and in other embodiments the spreading area 208 is defined by printing a patterned layer of a hydrophobic material, such as polytetrafluoroethylene (PTFE), onto the second surface 204 of the body 200 around/boarding the through bore 206.

It is to be appreciated that the driving force in the spreading area is a capillary action, having behavior known to one skilled in the art. The capillary action relies upon surface energies of the spreading area, plus properties of the blood sample such as viscosity and surface tension, but also depends upon the geometry and spacing of the through bore 206 and spreading area 208 surfaces. The spreading area 208 does not consist of microchannel structures, although those may be used if desired in other embodiments. Surfactants may also adjust the surface tension of the provided sample, such as to increase spreading. An example of a surfactant is the group of Fluorad™ surfactants from 3M Corporation of St Paul, Minn. Silicic acid or detergant types are other such examples.

It is to be appreciated that the spreading area 208 functions to evenly distribute the blood sample into a layer, and as such the spreading of the sample also depends on the amount of the transported sample. In that regard, the amount of the body fluid sample reaching the spreading area 208 for spreading is typically in the range of about 10 to about 90% of the sample transported via the blood transport portion 92, which is an amount that suitably spreads in the detection area of the test pad 39 for detection by LED-photodiode detection techniques.

Elongated Body

Figures 4, 6, 7, 8:
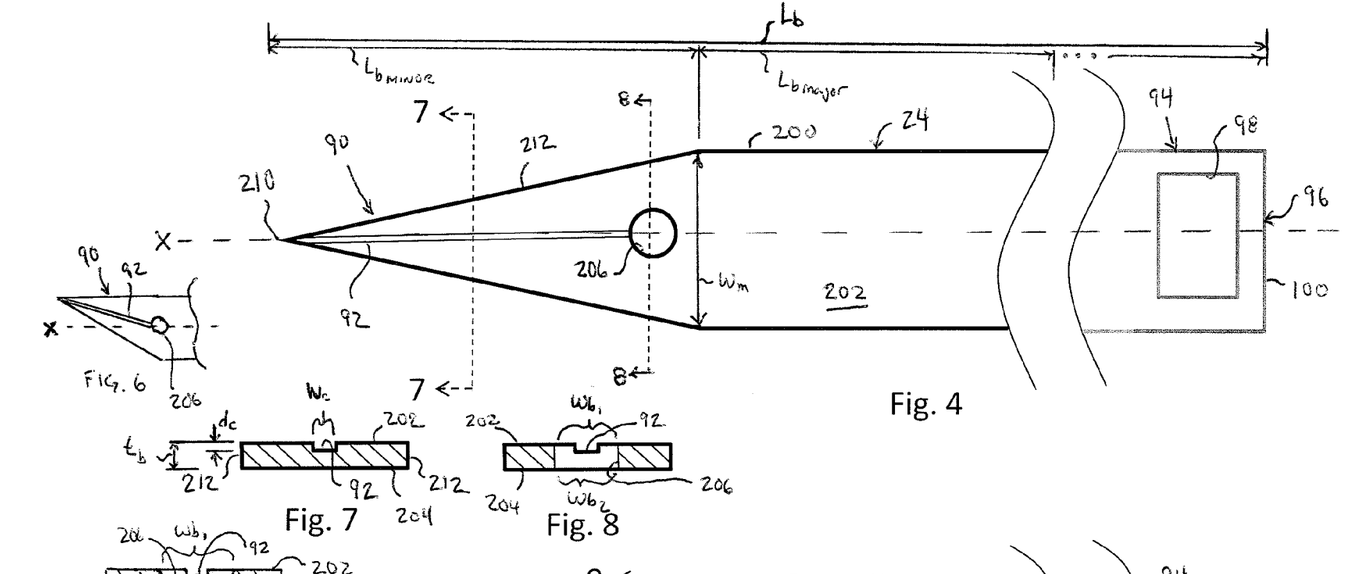
FIG. 4 illustrates a top view of another embodiment of a lancet structure suitable for use in the lancet compartment of FIG. 3.
FIG. 6 illustrates a top view of another embodiment of a lancet structure suitable for use in the lancet compartment of FIG. 3, the bottom view having similar features as depicted in FIG. 5.
FIG. 7 illustrates a cross-sectional view of the lancet structure of FIG. 4 taken along section line 7-7.
FIG. 8 illustrates a cross-sectional view of the lancet structure of FIG. 4 taken along section line 8-8.

In the illustrated embodiment, the elongated body 200 is a single, planar material layer. In some embodiments, the elongated body 200 has a substantially uniform thickness $t_b$ as is depicted in cross-section by FIG. 7. In some embodiments, the thickness $t_b$ can range from about 0.07 to about 0.5 mm. As also depicted by FIG. 7, the first and second surface 204 are separated by a side surface 212. In some embodiments, the side surface 212 can be shaped as a knife edge at least about a portion of the skin penetrating end 90 as depicted in FIG. 3. In some embodiments, the side surface 212 is shaped as a knife edge via a bevel. In other embodiments, the side surface 212 is shaped as a knife edge via one of the surfaces 202 or 204 tapering inwards. In some embodiments, the side surface 212 is shaped as a knife edge via the side surface 212 coming to a pointed side end.

As shown by FIG. 4, the elongated body 200 has a major (first) width $w_m$ which narrows or tapers down to a point tip 210 to form the skin penetrating end 90. In some embodiments, the major width $w_m$ can range from about 0.2 to about 0.6 mm. In one embodiment, the elongated body 200 has a length $L_b$, wherein a major (or majority) length $L_{bmajor}$ of the elongated body 200 has substantially the major width $w_m$, and wherein the elongated body 200 narrows from the major width $w_m$ down to the pointed tip over a remaining minor (or minority) length $L_{bminor}$ of the elongated body 200 to define the skin penetrating end 90. In some embodiments, length $L_b$ can range from about <1 to about 5 cm, wherein the minor length $L_{bminor}$ can range from about 1% to about 30% of length $L_b$. In other embodiments, the major length $L_{bmajor}$ is in the range from about 6 to about 12 mm, and in still other embodiments the minor length $L_{bminor}$ is in the range from about 1 to about 2.5 mm. It is to be appreciated that in some embodiments, $L_{bmajor}+L_{bminor}=L_b$, and in other embodiments, $L_{bmajor}+L_{bminor}\neq L_b$, in which the remainder of the length of the elongated body 200 may be provided by the connecting structure 94 or other lancet end feature, which may or may not have the same width and thickness as the major length $L_{bmajor}$.

In the illustrated embodiment of FIG. 4, the through bore 206 and the blood transport portion 92 are provided in portion of the body 200 defined by the minor length $L_{bminor}$. In other embodiments, the through bore 206 may be provided in the portion of the body 200 defined by the major length $L_{bmajor}$. In still other embodiments, the through bore 206 may be provided partially in both portions of the body 200 defined by the major and minor lengths $L_{bmajor}$, $L_{bminor}$.

Blood Transport Portion

In some embodiments, the skin penetrating end 90 has mirror-image symmetry about a longitudinal axis X (FIG. 4) such that the blood transport portion 92 extends substantially along the longitudinal axis X from the skin penetrating end 90 to the through bore 206. In other embodiments, such as depicted by FIG. 6, the skin penetrating end 90 does not have mirror-image symmetry about the longitudinal axis X. In such embodiments, the blood transport portion 92 then extends transverse to the longitudinal axis X from the skin penetrating end 90 to the through bore 206. In some embodiments, the shape of the path and dimensions of the blood transport portion 92 may be chosen such that blood sample is able to freely flow through the blood transport portion from the incision to the through bore 206. In some embodiments, the shape of the path and dimension of the blood transport portion 92 may depend on a desired flow rate of the blood sample to the through bore 206 and second surface 204. In some embodiments, the flow rate provided by the blood transport portion 92 is in the range of about 200 to about 500 nl/s, and in other embodiments the flow rate is about 360 nl/s (i.e., a 90 nl sample filling in about 250 ms). In some embodiments, the blood transport portion 92 has a length $L_c$ ranging from about 1 to about 8 mm.

The formation of the blood transport portion 92 can result from deposition, such as photolithographic patterning, molding, printing, stamping embossing or etching into the body 200, or other patterning methods known to one skilled in the art. For example, in some embodiments, the blood transport portion 92 is defined by etching into the body 200 a micro groove and in other embodiments the blood transport portion 92 is defined by printing a patterned layer of a hydrophobic material, such as polytetrafluoroethylene, onto the first surface 202 of the body 200 to define (via boarding) a channel from the pointed tip 210 to and in some embodiments around (i.e., boarding) the through bore 206.

In the embodiments where the blood transport portion 92 is a micro groove provided in the first surface 202, the micro groove has a depth $d_c$ ranging from about 40 to about 100 microns, and width $w_c$ ranging from about 70 to about 150 microns as depicted in cross-section by FIG. 7. In some embodiments, at least one of the blood transport portion 92 and the through bore 206 can be treated to be hydrophilic. In still other embodiments, portions of the first surface 202 which borders the blood transport portion 92 and the through bore 206 can be treated to be hydrophobic if desired.

Through Bore

In some embodiments, the shape and size of the through bore 206 depends on a desired flow rate of the bodily fluid to the second surface 204. In some embodiments, the flow rate through the through bore is in the range from about 200 to about 500 nl/s. In some embodiments, the through bore 206 has a perimeter shape selected from circular, oval, rectangular, square, triangular and polygonal. In still other embodiments, the through bore 206 has a perimeter shape selected from circular, oval, rectangular, square, triangular, polygonal and other non-circular shapes on the first surface 202, and on the second surface 204, the through bore 206 has a perimeter shape selected from circular, oval, rectangular, square, triangular, polygonal and other non-circular shapes. In some embodiments, the through bore 206 has a first width $w_{b1}$ on the first surface 202 and a second width $w_{b2}$ of the second surface 204 as depicted by FIG. 8. In some embodiments, the second width $w_{b2}$ is substantially the same as the first width $w_{b1}$. In other embodiments, the through bore 206 changes from the first width $w_{b1}$ on the first surface 202 to the second width $w_{b2}$ of the second surface 204 as depicted by FIG. 10. In some embodiments, the first width $w_{b1}$ is larger than the second width $w_{b2}$. In other embodiments, the first width $w_{b1}$ is smaller than the second width $w_{b2}$ such as depicted in FIG. 9. In some embodiments, the through bore 206 has a cross-sectional configuration cylindrical or polygonal cross-sectional configuration. In some embodiments, in which the spreading area 208 is provided adjacent the through bore 206, the through bore 206 can be provided with a partial step in diameter or width to form the spreading area 208 as also depicted by FIG. 9. In some embodiments the first and second widths $w_{b1}$, $w_{b2}$ are diameters. In some embodiments, the through bore 206 has a first end portion adjacent the first surface 202 which has a larger diameter than a second end portion adjacent the second surface 204 as depicted by FIG. 10 or vice versa (not shown).

The flow of the bodily fluid may be enhanced along the blood transport portion 92 and/or through the through bore 206 by modifying the surfaces of those features to be hydrophilic. In still other embodiments, the outlining surfaces of the body 200 bordering such features may also be modified to be hydrophobic to enhance containment of the bodily fluid to the blood transport portion 92 and/or the through bore 206. Such a surface modification may be achieved using mechanical, chemical, corona discharge and/or plasma treatment. Examples of such coatings and methods are marketed by AST Products (Billerica, Mass.) and Spire Corporation (Bedford, Mass.).

Figure 11:
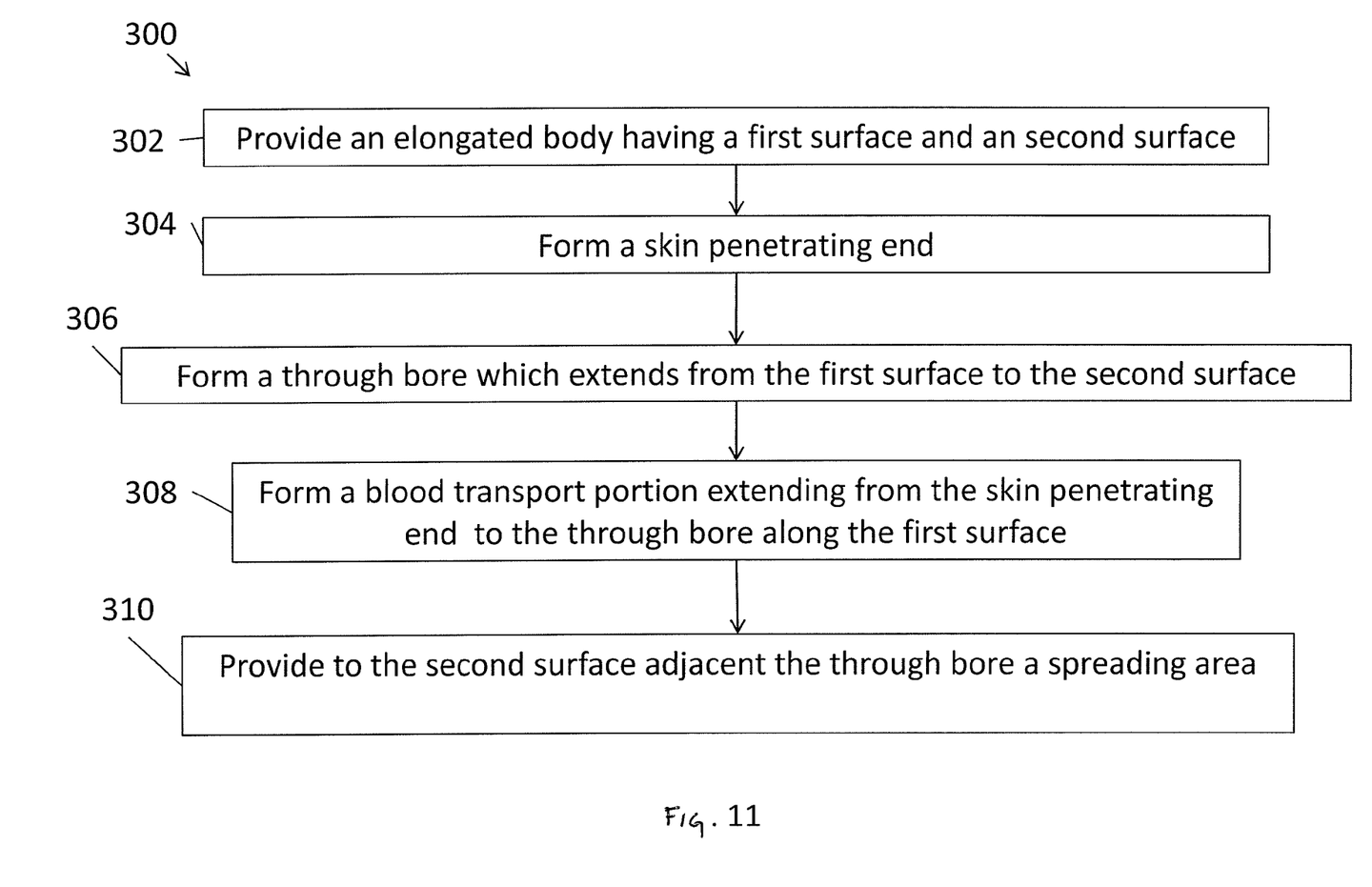
FIG. 11 is a flow chart illustrating a method of forming a lancet structure which is used for making an incision at a skin site and transporting an amount of blood from the incision away from the skin site.

In another embodiment, a method 300 for forming a lancet structure 24 for making an incision at a skin site and transporting an amount of bodily fluid from the incision away from the skin site is disclosed by FIG. 11. The method 300 comprises providing in step 302 an elongated body 200 having a first surface 202 and an second surface 204, and forming in step 304 a skin penetrating end 90 for making the incision in the body 200. The method 300 also comprises forming in step 306 a through bore 206 which extends from the first surface 202 to the second surface 204, and forming in step 308 a blood transport portion 92 extending from the skin penetrating end 90 to the through bore 206 along the first surface 202. The blood transport portion 92 is configured to transport the amount of bodily fluid away from the skin site via a capillary force to the through bore 206, and the through bore 206 is configured to transport the bodily fluid to the second surface 204 also via a capillary force. Lastly, in some embodiments, the method 300 includes providing in step 310 to the second surface adjacent the through bore 206, a spreading area 208 for increasing the surface area of the blood sample transported to the second surface 204 via the through bore 206.

In some embodiments of the method 300, the skin penetrating end 90 is formed by mechanically working the body 200 to have a pointed end. In other embodiments, the through bore 206 is formed by laser drilling the body 200. In other embodiments, the blood transport portion 92 is formed by laser etching the body 200 to form a microgroove in the first surface 202. In still other embodiments, the blood transport portion 92 and the through bore 206 may be fabricated by assembled together by e.g., gluing or fusing, a number of material layers. For example, each material layer can have a through hole on a single piece of solid substrate material in which the assembled layers together form the through bore 206. At least a top material layer (i.e., the layer which has the first surface 202) which in addition to providing a top portion of the through hole 206 also provides a slot to define the side walls of the blood transport portion 92, the bottom being defined by a lower material layer(s) when assembled together. A bottom material layer (i.e., the layer which has the second surface 204) may provide a through hole which aligns with the other through hole(s) of the other upper material layer(s), but also which defines or provides the spreading area 208 that is provided adjacent the through bore 206. The fabrication methods used to form the lancet structure 24 may include mechanical drilling or chemical/electrochemical etching by methods known in the art to form the blood transport portion 92, the through bore 206 and/or the spreading area. Another method uses a precision molding process to produce the lancet structure using known techniques. The material layer(s) of the body 200 can be metal, ceramic, plastic, polymer or other suitable materials such as composites thereof.

Method of Concentrating a Blood Sample on a Test Pad

Figure 12:
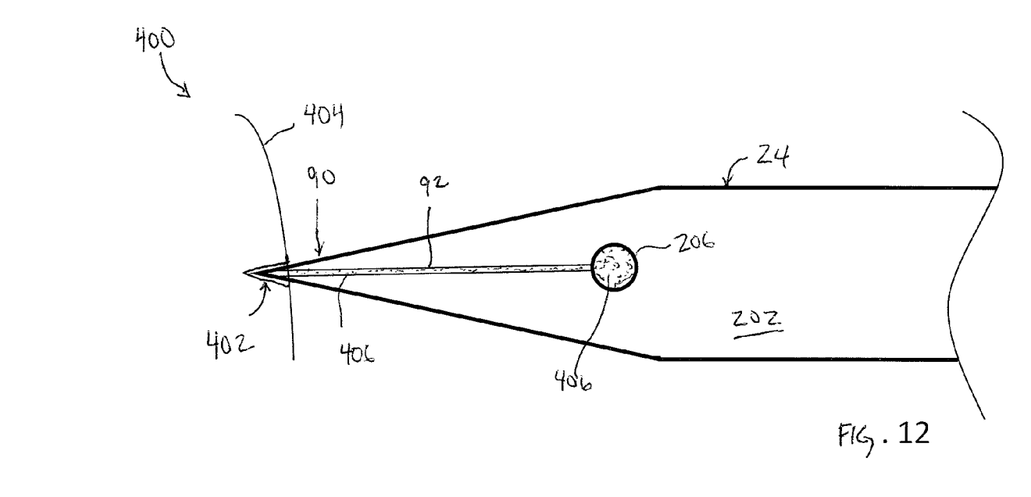
FIG. 12 illustrates a top view of an embodiment of a lancet structure being used to transport an amount of blood away from an incision (made thereby) at a skin site from a first surface to a second surface via a through bore.
Figure 13:
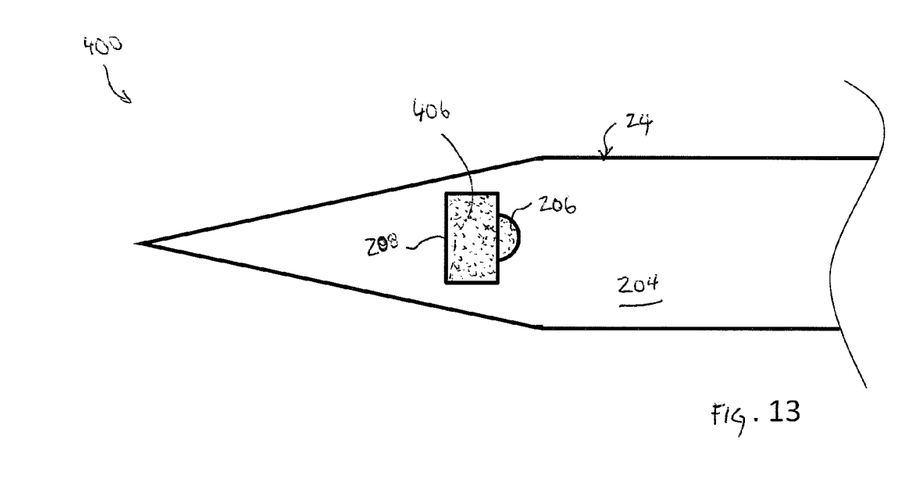
FIG. 13 illustrates a bottom view of the embodiment of the lancet structure of FIG. 12 showing the blood sample being transported to the second surface and spread out according to one embodiment to concentrate the blood sample thereon for contact with a test pad.

With reference to FIGS. 12-13, a method 400 of concentrating a blood sample on a test pad is also disclosed. The method 400 comprising utilizing a lancet structure 24 according one of the above described embodiments of the invention to make an incision 402 at a skin site 404 and transporting an amount of a blood sample 406 from the incision away from the skin site. In particular, the blood sample 406 is transported along the first surface of the lancet structure 24 by the blood transport portion 92 from the incision 402 to the through bore 206 via a capillary force. Upon arriving at the perimeter of the through bore 206 on the first surface 202, a capillary force then transports the blood sample 406 through the through bore 206 to the second surface 204 of the lancet structure 24. Upon arriving at the second surface 204, in the illustrated embodiment of FIG. 13, a capillary force spreads the blood sample to occupy the boundaries defined by the geometry of the spreading area 208. At this point, as the blood sample is spread out and providing a large surface area, the blood sample then can be contacted with a test pad, such as test pad 39 (FIG. 3) as discussed previously above in earlier sections.

It is to be appreciated that the embodiments disclosed herein can be useful to help facilitate blood glucose or similar detection in "one-step", such as performed by the previously mentioned medical diagnostic device described in the co-pending and commonly owned U.S. patent application Ser. No. 12/981,677, filed Dec. 30, 2010, and entitled HAND- HELD MEDICAL DIAGNOSTIC DEVICES. It is also to be appreciated that the transfer of the drawn liquid sample (e.g., blood) from the first surface to the second surface of the lancet via the capillary action of the blood transport portion in certain embodiments momentarily keeps the liquid sample on the first surface such that as the lancet is drawn back into a housing, such as the lancet compartment, upon which the second surface of the lancet may slide or otherwise touch, the sample will neither be wiped from nor be interfered with during transport. It is further to be appreciated that in certain embodiments the spreading area of the lancet could be filled after contact with the test pad is made. In such an embodiment, the drawn liquid sample (e.g., blood) would reach the second surface at the through bore and wait until contact is made with the test pad. After contact, with the test pad acting as a second capillary forming element, the liquid sample would then fill the spreading area, displacing any air bubbles by laminar flow which could be formed by dropping the unfilled spreading area flat against the test pad as previously described.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A lancet structure for making an incision at a skin site and transporting an amount of blood from the incision away from the skin site, the lancet structure comprising an elongated body having a first surface and a second surface, a skin penetrating end for making the incision, a through bore extending from the first surface at an area of ingress of the through bore to the second surface at an area of egress of the through bore, a blood transport portion extending from the skin penetrating end to the through bore along the first surface, and a spreading area adjacent the through bore for increasing the surface area of the blood fluid transported to the second surface via the through bore, the spreading area being provided only in the second surface and in communication with the through bore, the blood transport portion being configured to transport the amount of blood away from the skin site via a capillary force to the through bore, and the through bore being configured to transport the blood to the second surface spreading area, the spreading area extending outwardly beyond the area of egress of the through bore for increasing the surface area of the blood fluid beyond the area of egress of the through bore, the through bore intersecting the second surface at a location partially outside the spreading area.

2. The lancet structure according to claim 1 wherein the elongated body is a single, planar material layer.

3. The lancet structure according to claim 1 wherein the elongated body has a first width which narrows down to a point tip to form the skin penetrating end.

4. The lancet structure according to claim 1 wherein the elongated body has a length, wherein the majority of the length of the elongated body has substantially a first width, and wherein the elongated body narrows from the first width down to a pointed tip over a remaining minority of the length of the elongated body to define the skin penetrating end.

5. The lancet structure according to claim 4 wherein the through bore and the blood transport portion are provided in the minority of the length.

6. The lancet structure according to claim 4 wherein the majority of the length is in a range from 6 to 12 ram, and wherein the minority of the length is in a range from 1 to 2.5 ram.

7. The lancet structure according to claim 1 wherein the elongated body has a substantially uniform thickness.

8. The lancet structure according to claim 7 wherein the thickness is in a range from 0.07 to 0.5 rm.

9. The lancet structure according to claim 1 wherein the elongated body is a material selected from metal, polymer, ceramic, and composites or laminates thereof.

10. The lancet structure according to claim 1 wherein the elongated body further comprises a connecting structure located at an end that is opposite the skin penetrating end.

11. The lancet structure according to claim 1 wherein the first and second surface are separated by a side, wherein the side provides a knife-edge at least about a portion of the skin penetrating end.

12. The lancet structure according to claim 1 wherein the skin penetrating end provides a knife edge.

13. The lancet structure according to claim 1 wherein the skin penetrating end has mirror-image symmetry about a longitudinal axis of the elongated body.

14. The lancet structure according to claim 1 wherein the skin penetrating end does not have mirror-image symmetry about a longitudinal axis of the elongated body.

15. The lancet structure according to claim 1 wherein a shape and size of the through bore depends on a desired flow rate of the blood to the second surface.

16. The lancet structure according to claim 15 wherein the flow rate is 360 nl/s.

17. The lancet structure according to claim 1 wherein the through bore has a perimeter shape selected from circular, oval, rectangular, square, triangular and polygonal.

18. The lancet structure according to claim 1 wherein on the first surface the through bore has a perimeter shape selected from circular, oval, rectangular, square, triangular and polygonal.

19. The lancet structure according to claim 1 wherein on the second surface the through bore has a perimeter shape selected from circular, oval, rectangular, square, triangular and polygonal.

20. The lancet structure according to claim 1 wherein the through bore tapers from a first width on the first surface to a second width of the second surface.

21. The lancet structure according to claim 20 wherein the second width is larger than the first width or smaller than the first width.

22. The lancet structure according to claim 1 wherein the through bore has a cross-sectional configuration cylindrical or polygonal cross-sectional configuration.

23. The lancet structure according to claim 1 wherein the blood transport portion extends substantially along a longitudinal axis from the skin penetrating end to the through bore.

24. The lancet structure according to claim 1 wherein the blood transport portion extends transverse to a longitudinal axis from the skin penetrating end to the through bore.

25. The lancet structure according to claim 1 wherein a shape and size of the blood transport portion depends on a desired flow rate of the blood to the second surface.

26. The lancet structure according to claim 25 wherein the flow rate is in a range from 200 to 500 nl/s.

27. The lancet structure according to claim 1 wherein the blood transport portion is a micro groove provided in the first surface.

28. The lancet structure according to claim 27 wherein the micro groove has a length ranging from 1 to 8 ram, a depth ranging from 40 to 100 microns, and a width ranging from 70 to 150 microns.

29. The lancet structure according to claim 1 wherein at least one of the blood transport portion and the through bore is treated to be hydrophilic.

30. The lancet structure according to claim 1 wherein portions of the first surface which borders the blood transport portion and the through bore are treated to be hydrophobic.

31. The lancet structure according to claim 1 wherein the amount of the blood is about 90 nanoliters (0.09 mm$^3$) or less.

32. A method of making an incision at a skin site and transporting an amount of blood from the incision away from the skin site comprising utilizing the lancet structure of claim 1.

33. A method of forming a lancet structure which is used for making an incision at a skin site and transporting an amount of blood from the incision away from the skin site, the method comprising: providing an elongated body having a first surface and a second surface; forming a skin penetrating end for making the incision in the body; forming a through bore which extends from the first surface at an area of ingress of the through bore to the second surface at an area of egress of the through bore; forming a blood transport portion extending from the skin penetrating end to the through bore along the first surface, the blood transport portion being configured to transport the amount of blood away from the skin site via a capillary force to the through bore, and the through bore being configured to transport the blood to the second surface; and providing in only the second surface adjacent in communication with the through bore a spreading area, the spreading area extending outwardly beyond the area of egress of the through bore for increasing the surface area of the blood fluid transported to the second surface via the through bore, the through bore intersecting the second surface at a location partially outside the spreading area.

34. The method of claim 33 wherein the skin penetrating end is formed by mechanical working the body to have a pointed end.

35. The method of claim 33 wherein the through bore is formed by laser drilling the body.

36. The method of claim 33 wherein the blood transport portion is formed by etching the body to form a microgroove in the first surface.

37. The method of claim 33 wherein the spreading area is provided to the second surface via etching.

\* \* \* \* \*

UNITED STATES PATENT AND TRADEMARK OFFICE
CERTIFICATE OF CORRECTION

| | |
|---|---|
| PATENT NO. | : 8,920,455 B2 |
| APPLICATION NO. | : 13/279399 |
| DATED | : December 30, 2014 |
| INVENTOR(S) | : Steven N. Roe |

It is certified that error appears in the above-identified patent and that said Letters Patent is hereby corrected as shown below:

Claims

Col. 14, Claim 6, Lines 2-4,
 "majority of the length is in a range from 6 to 12 ram, and wherein the minority of the length is in a range from 1 to 2.5 ram." should read
 --majority of the length is in a range from 6 to 12 mm, and wherein the minority of the length is in a range from 1 to 2.5 mm.--;

Col. 14, Claim 8, Line 8,
 "thickness is in a range from 0.07 to 0.5 rm." should read
 --thickness is in a range from 0.07 to 0.5 mm.--;

Col. 15, Claim 28, Line 2,
 "micro grove has a length ranging from 1 to 8 ram, a depth" should read
 --micro grove has a length ranging from 1 to 8 mm, a depth--; and Col. 16, Claim 34, Line 15,
 "end is formed by mechanical working the body to have a" should read
 --end is formed by mechanically working the body to have a--.

Signed and Sealed this
Eighth Day of December, 2015

Michelle K. Lee
*Director of the United States Patent and Trademark Office*